United States Patent [19]

Maiese et al.

[11] Patent Number: 5,519,035
[45] Date of Patent: May 21, 1996

[54] TREATMENT OF STROKE OR IN ANTICIPATION OF THE OCCURRENCE OF BRAIN ISCHEMIA

[75] Inventors: Kenneth Maiese; John A. Wagner, both of New York, N.Y.

[73] Assignee: Cornell Research Foundation, Inc., Ithaca, N.Y.

[21] Appl. No.: 84,977

[22] Filed: Jul. 2, 1993

[51] Int. Cl.$^6$ .................................................. A61K 31/47
[52] U.S. Cl. ........................ 514/309; 514/369; 514/211; 514/279; 514/253
[58] Field of Search .................................. 514/211, 279, 514/253, 309, 369

[56] References Cited

U.S. PATENT DOCUMENTS

| | | | |
|---|---|---|---|
| 4,940,694 | 7/1990 | della Valle et al. | 514/25 |
| 5,204,370 | 4/1993 | Jiang et al. | 514/475 |
| 5,266,594 | 11/1993 | Dawson et al. | 514/560 |
| 5,344,841 | 9/1994 | Jiang et al. | 514/549 |

FOREIGN PATENT DOCUMENTS 0446699  9/1991  European Pat. Off.

OTHER PUBLICATIONS

AN 111:90221. Joo, F., et al, "Inhibition by H-7 of the Protein Kinese C Prevents Formation of Brain Edema in Sprague–Dawley CFY rats", *Brain Research* (1989), 490(1), 141–143.

Hara, H., et al, "Staurosporine, a Novel Protein Kinase C Inhibitor, Prevents Neuronal Damage in the Gerbil and Rat", *J. Cereb. Blood Flow Metab.* (1990), 10(5), 646–653, Chem. Abstract AN 114:480 CA.

Ohono et al, "Effect of Staurosporine, a PKC Inhibitor, on Impairment of Working Memory in Rats Exposed to Cerebral Ischemia", *Eur. J. Pharm* 29 Oct. 1991 204(1) 113–6. AN 92209620.

Nixon, J. S., et al, Agents and Actions, 32, 3/4, 188–193 (1991).

Hannun, Y. A., et al, J. Biol. Chem., 261, 12604–12609 (1986).

Kawamoto, S., et al, Biochem. Biophys. Res. Commun. 125, 258–264 (1984).

Program for International Meeting on Microcirculatory Stasis in the Brain, Tokyo, Japan, May 20–21, 1993.

Program for International Symposium on Cerebral Blood Vessel '93, Mt. Zao, Japan, May 28–30, 1993.

Mattson M., Experimental Neurology, 112, 95–103 (1991).

Nakane, M., et al, Biochem. Biophys. Res. Commun, 180, 1396–1402, Nov. 1991.

Knowles, R. G., et al, Biochem J., 269: 207–210 (1990).

Nowicki, J. P., et al, Euro. J. Pharm. 204, 339–340 (1991).

Dawson, V. L., et al, Proc. Natl. Acad. Sci, USA 88, 6368–6371 (1991).

Endoh, M., et al, Neuroscience letters 154, 125–128 (1993).

Favaron, M., et al, Proc. Natl. Acad. Sci. USA 85, 7351–7355 (Oct. 1988).

Lancaster, J. R., American Scientist, 80, 248–257 (May–Jun. 1992).

Mattson et al, M. P., et al, The Journal of Neuroscience, 8(6), 1087–2100 (Jun. 1988).

Sato, S., Biochimica et Biophysica Acta, 1181, 195–197 (1993).

Bredt, D. S., et al, Proc. Natl. Acad. Sci. USA, vol. 86, 9030–9033, Nov. 1989.

Bredt, D. S., et al, The Journal of Biological Chemistry, vol. 267, No. 16, 10976–10981, Jun. 1992.

Favaron, M., et al, Proc. Natl. Acad. Sci. USA, vol. 87, 1938–1987, Mar. 1990.

Garthwaite, J., et al, European Journal of Pharmacology—Molecular Pharmacology Section, 172, 413–416 (1989).

Hidaka, H., et al, Biochemistry, 23, 5036–5041, 1984.

Knowles, R. G., Proc. Natl. Acad. Sci. USA, vol 86, 5159–5162, Jul. 1989.

Maiese, K., et al, Soc. Neurosci. Abst., 18(2), 1453, presented Oct. 30, 1992.

Maiese, K., et al, Presentation at International Meeting on Microcirculatory Stasis, Tokyo, Japan, May 20, 1993, entitled "Down–Regulation of Protein Kinase C is Neuroprotective During Nitric Oxide Toxicity".

McKenna et al, U.S. Statutory Invention Registration H1168, published Apr. 6, 1993.

Rothman, S. M., et al, Annals of Neurology, vol. 19, No. 2, Feb. 1986, pp. 105–111.

*Primary Examiner*—Marianne M. Cintins
*Assistant Examiner*—Keith MacMillan

[57] ABSTRACT

Administration of protein kinase C inhibitors protect neuronal cells from death from cerebral ischemia. Model for screening compounds for potential for protecting neuronal cells from death from cerebral ischemia comprises adding the compounds to medium containing neuronal cells before, at the same time as, and/or after nitric oxide administration.

5 Claims, 1 Drawing Sheet

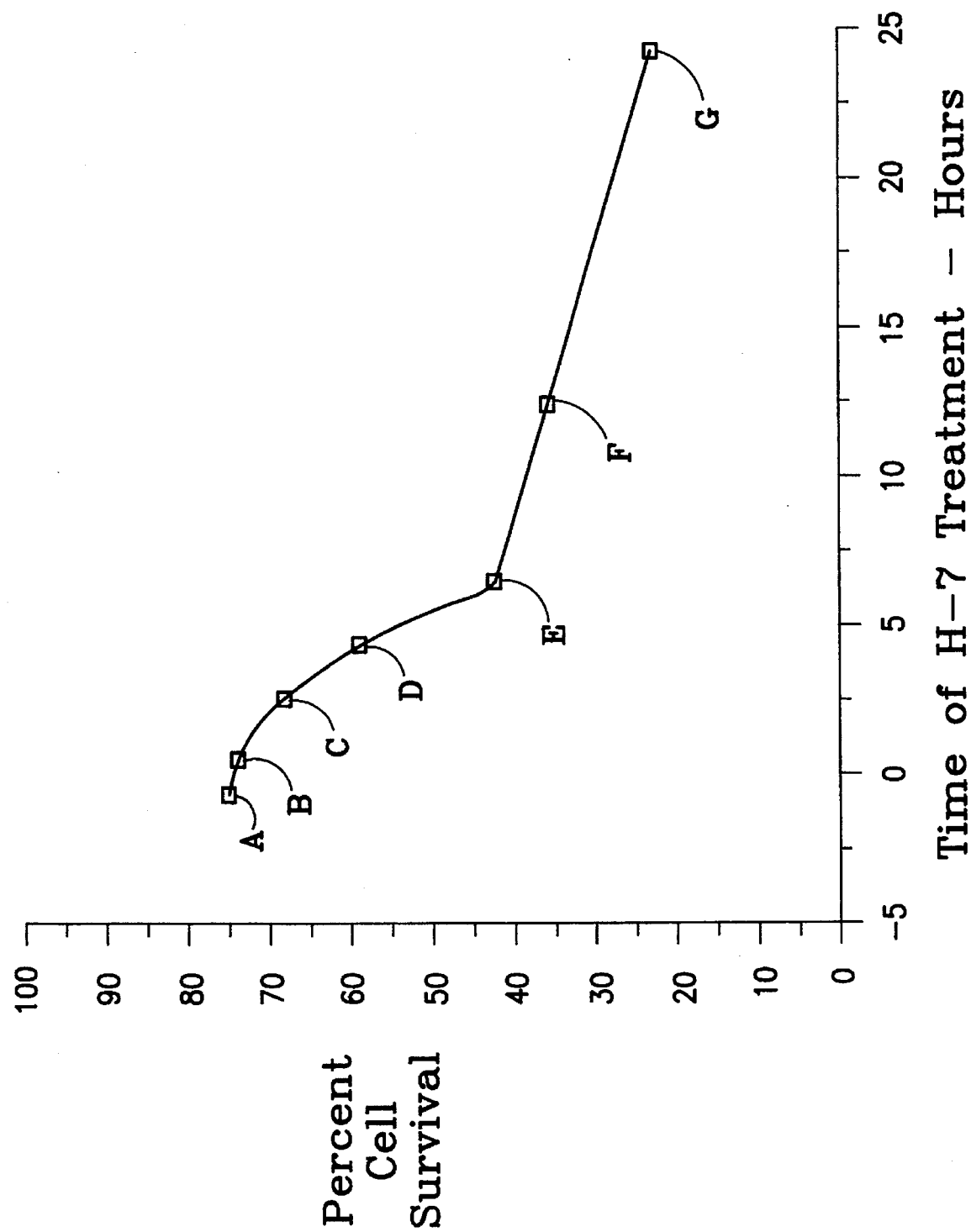

TREATMENT OF STROKE OR IN ANTICIPATION OF THE OCCURRENCE OF BRAIN ISCHEMIA

This invention was made at least in part with Government support under Grants NINDS K08-NS-01599 and NEI EY0654, from the National Institutes of Health.

TECHNICAL FIELD

This invention is directed to reducing the neurological dysfunction normally occurring in a stroke.

BACKGROUND OF THE INVENTION

Strokes are the third largest killer of people in the United States and cost billions of dollars because of lost productivity and the need for rehabilitation. Many of those affected with strokes never recover full neurologic function or even a substantial measure of the neurologic function initially lost.

Presently, treatment consists of attention to and maintenance of blood pressure and serum glucose, administration of IV fluids and prevention of the occurrence of bed sores. Sometimes blood thinners such as heparin are administered during the course of a stroke but there is no support for this having any palliative effect.

SUMMARY OF THE INVENTION

It is an object of the invention herein to provide a method of treating subjects with strokes or who are of high risk for a stroke because of having experienced a previous ischemic event, to reduce the occurrence of neuronal damage and associated neurological dysfunction in a stroke compared to that which normally occurs. The method comprises administering to the subjects a therapeutically effective amount of a protein kinase C inhibitor, i.e., in the case of those with a stroke an amount of protein kinase C inhibitor which reduces the occurrence of neuronal damage and associated neurological dysfunction that would otherwise occur during a stroke and in the case of those who are of high risk for a stroke an amount of protein kinase C inhibitor which provides an uninterrupted plasma level of protein kinase C inhibitor which on the occurrence of cerebral ischemia will reduce the occurrence of neuronal cell damage and associated neurological dysfunction that would occur during a stroke.

We turn firstly to the case of a subject currently afflicted with a stroke. For such subject, therapy pursuant to the invention very preferably should occur as soon as diagnosis occurs, normally within 6 hours of the onset of the stroke. In order to obtain the fastest response, the administration of the protein kinase C inhibitor should be via a parenteral route and in a neuronal cell protecting amount, i.e., an amount which reduces neuronal cell death compared to that which would occur if the stroke were untreated.

We turn now to the case of a subject who is at high risk for a stroke because of having experienced a previous ischemic event, i.e., a previous transient ischemic attack, a previous residual ischemic neurological deficit or a previous completed stroke or a plurality of these or combinations of these, but who does not currently have a stroke in progress. For such subject, the requirement is to provide a plasma level of protein kinase C inhibitor such that, on the occurrence of cerebral ischemia, there will be sufficient protein kinase C inhibitor already present in the subject to protect neuronal cells, i.e., in an amount which would reduce neuronal cell death compared to that which would occur if a stroke occurred and was untreated. Administration is preferably carried out orally on a daily basis.

The term "subject" is used herein to mean mammals including humans.

BRIEF DESCRIPTION OF THE DRAWING

The single FIGURE of the drawing is a graph of time of treatment after initiation of conditions functioning as a model for stroke versus cell death for treatment with 10 µM H-7 in Example II.

DETAILED DESCRIPTION

As indicated above, the method herein comprises administering to a subject currently afflicted with a stroke or previously afflicted with an ischemic event, of a therapeutically effective amount of protein kinase C inhibitor.

Suitable protein kinase C inhibitors are those which are non toxic and include, for example, H-7, i.e., 1-(5-isoquinolinylsulfonyl)-2-methylpiperazine, H-8, i.e., N-[2-(methylamine)ethyl]-5-isoquinolinesulfonamide, sphingosine, staurosporine, 1-(5-isoquinolinylsulfonyl)-2,3-dimethylpiperazine, 1-(5-isoquinolinylsulfonyl)-3,5-dimethylpiperazine, N-(2-aminoethyl)-5-isoquinolinesulfonamide, N-(2-guanidinoethyl)-5-isoquinolinesulfonamide and N,N-dimethyl-5-isoquinolinesulfonamide. H-7 and H-8 are preferred with H-7 being most preferred. H-7 and H-8 are available from Calbiochem (La Jolla, Calif.). Sphingosine and staurosporine are available from Sigma Chemical Company (St. Louis, Mo.). Syntheses for the other listed compounds are described in Hidaka, H., et al, Biochemistry, 23, 5036–5041 (1984).

The therapeutically effective amount for those with a stroke is a neuronal cell protecting amount, i.e., an amount which reduces neuronal cell death compared to that which would occur if the stroke were untreated. Cells known to be killed during a stroke include hippocampal neurons, cortical neurons, caudate and putaminol neurons, cerebellar neurons and brain stem neurons. Since, of these, hippocampal neurons are known to be the most sensitive to strokes, the therapeutically effective amount is preferably a hippocampal neuron protecting amount, i.e., an amount which reduces hippocampal neuron death compared to that which would occur if the stroke were untreated. In general a therapeutically effective amount for those with a stroke is a non toxic amount in the range of 0.005 mg/kg to 100 mg/kg. For H-7, the dose preferably ranges from 1.5 mg/kg to 25 mg/kg and the very preferred dose normally ranges from 5 mg/kg to 10 mg/kg. Activities for various of the protein kinase C inhibitors are listed in Hidaka, H., et al, Biochemistry, 23, 5036–5041 (1984) and suitable dosages can be determined by multiplying the dosages of H-7 given above by the reciprocal of the relative activity of H-7 to that of the protein kinase C inhibitor for which dosage information is desired. For sphingosine, suitable dosages include from 5 to 20 mg/kg and for staurosporine suitable dosages include from 0.005 mg/kg to 1 mg/kg.

The therapeutically effective amount for those who are at high risk for a stroke because of having experienced a previous ischemic event but who do not currently have a stroke in progress, is one that provides a plasma level of protein kinase C inhibitor such that on occurrence of cerebral ischemia there will be sufficient protein kinase C inhibitor already present in the subject to protect neuronal cells, i.e., in an amount which will reduce neuronal cell death compared to that which would occur if a stroke occurred and was untreated. Since the occurrence of ischemia could come at any time, such plasma level must always be present, that is must be uninterrupted by reduction to a level where sufficient protein kinase C inhibitor is not present to protect neuronal cells from death on the occurrence of ischemia. In general, this plasma level of protein kinase C inhibitor is a non toxic concentration in the range of from about 0.001 µM to 100 µM. The amount administered to obtain such plasma level depends on the method of administration and the half-life of the particular protein kinase C inhibitor administered. Preferably, administration is on a daily basis so that each dose can be minimized. For H-7, orally administered, one time a day, a suitable dose might be 20 mg/kg.

We turn now to the methods of administration. This can be any method by which the protein kinase C inhibitor crosses the blood-brain barrier in sufficient amount to protect neuronal cells from death. Crossing the blood-brain barrier is typically not a problem for protein kinase C inhibitors as suggested by the pretreatment intraperitoneal administration of H-7 reducing brain edema in an in vivo stroke model (Joó, F., et al, Brain Research, 490, 141–143 (1989). For the case of a subject currently afflicted with a stroke in progress, parenteral administration is preferred in order to obtain a fast response, very preferably intravenous or intraarterial administration. For the case of a subject who is at high risk for a stroke because of having experienced a previous ischemic event but who does not currently have a stroke in progress, administration is preferably carried out orally so that the presence of a health care professional is not required.

We turn now to the time of administration. We turn firstly to those subjects with a stroke in progress. For those with a stroke, time is of the essence so administration very preferably should occur as soon as diagnosis occurs. Normally, to obtain benefit, administration should be within 6 hours of the onset of the stroke, preferably within 4 hours of the onset of the stroke. We turn now to those subjects who are at high risk for a stroke because of having experienced a previous ischemic event but who do not currently have a stroke in progress; administration is preferably on a daily basis for convenience and to minimize the dose at each administration.

We turn now to examples which illustrate the efficacy of the invention.

It is noted that nitric oxide has been implicated as a mediator of neurodegeneration in vivo models of cerebral ischemia (Nowicki, J. P., et al, Euro, J. Pharm., 204:339–340 (1991)). Furthermore, work by the inventors herein in vitro indicates that hippocampal neuronal death following anoxia is at least in part mediated by nitric oxide, that nitric oxide generated by sodium nitroprusside and by 3-morpholino-sydnonimine was toxic to hippocampal neurons and that it is the nitric oxide from the nitroprusside and not cyanide that causes cell death. On this basis, the inventors herein have devised a method for the in vitro assessment of potential of drugs for effectiveness in protecting hippocampal neurons from death mediated by the presence of nitric oxide which constitutes an in vitro model for screening drugs for efficacy in protecting neuronal cells from death during cerebral ischemia including strokes. This testing method comprises the steps of forming a culture of neuronal cells in a medium, e.g., $1\times10^4$ to $1\times10^6$ cells/mm², administering nitric oxide generating agents (e.g., using a source of nitroprusside or SIN-1 (i.e., 3-morpholino-sydnonimine)) to the neuronal cells in a fresh culture medium, replacing the culture medium to prevent further nitric oxide administration (e.g., 3 to 15 minutes after nitric oxide administration is initiated), before, at the same time as, and/or after the administering of nitric oxide adding compound to be tested to culture medium containing the cells, and assessing neuronal cell death.

In examples, compounds were evaluated for protecting neuronal cells from death during cerebral ischemia by the specific execution of said testing method which is set forth below.

Hippocampi were obtained from one day old Sprague-Dawley rat pups and maintained by the method described in Furshpan, E. J., et al, Neuron 3:199–207 (1989) except that Sprague-Dawley rats were used instead of Long-Evans rats. Hippocampal sections were then incubated in a solution of papain (10 U/ml), cysteine (3 mmol/l), and dissociation medium for two 20 minutes periods. The hippocampi were then rinsed in dissociation medium and incubated in a solution of trypsin inhibitor (10–20 U/ml) and dissociation medium for three times, 5 min. each. The cells were washed in growth medium three times, two minutes each, and triturated 50 times in two ml of growth medium. The trituration was repeated five times with fresh growth medium to yield a total of 10 ml of cell suspension. Forty milliliters of Opti-MEM-I (Gibco BRL, Gaithersburg, Mo.; consisting of a modification of MEM (Eagle's) with HEPES buffer, 2,400 mg/l sodium bicarbonate, hypoxanthine, thymidine, sodium pyruvate, L-glutamine, trace elements and growth factors, and phenol red reduced to 1.6 mg/l) was added to this cell suspension and the dissociated cells were plated at a density of approximately $15\times10^5$ cells/mm² in 35 mm² polylysine-laminin coated plates (Falcon Labware, Lincoln Park, N.J.). Cells were maintained in growth medium at 37° C. in a humidified atmosphere of 5% $CO_2$ and 95% room air. Following a two hour incubation period to allow for cell adhesion, culture medium was replaced with 1.5 ml of growth medium and the medium was subsequently replaced weekly. All experiments were performed with cultured neurons that had been in culture for two to three weeks. Non-neuronal cells, which were identified by morphology, accounted for less than 20% of the total cell population.

Dissociation medium contained 90 mM $Na_2SO_4$, 30 mM $K_2SO_4$, 5.8 mM $MgCl_2$, 0.25 mM $CaCl_2$, 10 mM kynurenic acid, and 1 mM HEPES with pH adjusted to 7.4. Growth medium consisted of Leibovitz's L-15 Medium (Gibco BRL, Gaithersburg, Md.) with 6% sterile rat serum (Bioproducts for Science, Indianapolis, Ind.), 150 mM $NaHCO_3$, 2.25 mg/ml transferrin, 2.5 µg/ml insulin, 10 nM progesterone, 90 µM putrescine, 15 nM selenium, 35 mM glucose, 1 mM L-glutamine, penicillin (50 U/ml), streptomycin (50 µg/ml), and vitamin mix. The vitamin mix contained L-proline (0.2M), L-cystine (0.025M), p-aminobenzoic acid (7.0 mM), vitamin B-12 (0.3 mM), inositol (11 mM), choline chloride (14.0 mM), fumaric acid (0.04M), coenzyme A (0.1 mM), d-biotin (8 µM), and DL-6,8-thiotic acid (0.5 mM).

Nitric oxide administration was performed by removing the culture medium using a pipette and adding fresh growth medium containing 300 µM sodium nitroprusside (Sigma Chemicals Company, St. Louis, Mo.). After 5 to 10 minutes the culture medium was replaced with fresh growth medium, and the cultures were placed in a normal oxygen environment, humidified incubator at 37° C. with 5% $CO_2$ for 24 hours prior to assessing cell death.

In the case where the compound tested is administered starting before nitric oxide administration, it is also included in the fresh growth medium containing sodium nitroprusside and in the fresh growth medium replacing this. In the case where the compound tested is administered at the same time as nitric oxide is administered, it is later included in the fresh growth medium containing sodium nitroprusside and also in the fresh growth medium replacing this.

Hippocampal neuronal injury was determined by bright field microscopy using a 0.4% trypan blue dye exclusion method 24 hours following treatment with nitric oxide. Neurons were identified by morphology. The mean survival was determined by counting 8 randomly selected non-overlapping fields with approximately 10–20 neurons (viable+non-viable) in each 35 mm petri dish. The mean survival from each culture dish represents an N=1 determination. Each experiment was replicated 3–5 times independently on separate occasions with different cultures.

We turn now to the examples relying on this in vitro method to show efficacy for protein kinase C inhibitors in the treatment method herein.

EXAMPLE I

Hippocampal neuronal cultures were treated with H-7 at doses of 0.001 µM, 0.01 µM, 1.0 µM, 10 µM and 100 µM starting one hour prior to exposure to sodium nitroprusside or with no H-7. Without H-7 the neuronal cell survival rate was about 22%. With doses of H-7 of 0.001 µM, 0.01 µM and 0.1 µM, the survival rate increased to about 45%. At doses of 10 µM and 100 µM, the survival rate increased to about 63%. Administration of H-7 without nitric oxide showed H-7 was not toxic to the hippocampal cells except at the dose of 100 µM where survival decreased from 90% to 63%.

EXAMPLE II

Hippocampal neuronal cultures were treated with H-7 at doses of 10 µM, starting 1 hour prior to treatment with sodium nitroprusside, starting at the same time as sodium nitroprusside administration, starting 1 hour after sodium nitroprusside administration, starting 4 hours after sodium nitroprusside administration, starting 6 hours after sodium nitroprusside administration, starting 12 hours after sodium nitroprusside administration and starting 24 hours after sodium nitroprusside administration. In the case of administration at the same time as sodium nitroprusside, it was also included in the fresh growth medium replacing the culture medium with sodium nitroprusside. Results are shown in the FIGURE of the drawing. For treatment starting 1 hour before (A in the FIGURE of the drawing) and treatment starting at the same time as sodium nitroprusside administration (B in the FIGURE of the drawing), neuronal cell survival rate was about 75% compared to about 68% for treatment starting 1 hour after sodium nitroprusside administration (C in the FIGURE of the drawing), about 60% for treatment starting 4 hours after sodium nitroprusside administration (D in the FIGURE of the drawing), about 40% for treatment starting 6 hours after sodium nitroprusside administration (E in the FIGURE of the drawing), about 35% for treatment starting 12 hours after sodium nitroprusside administration (F in the FIGURE of the drawing) and about 22% for treatment starting 24 hours after sodium nitroprusside administration (G in the FIGURE of the drawing) and about 22% where no H-7 is added.

EXAMPLE III

Hippocampal neuronal cultures were treated with H-8 at doses of 0.001 µM, 0.01 µM, 1.0 µM, 10 µM and 100 µM starting 1 hour prior to exposure to sodium nitroprusside or with no H-8. H-8 was not toxic to the neuronal cells at any of the concentrations. Survival with only administration of sodium nitroprusside (nitric oxide) was 46+2%. Significant protection with H-8 was initially present with doses of 0.01 µM (60+5% survival) and maximum survival (about 80%) occurred at doses of 10 µM and greater.

EXAMPLE IV

Hippocampal neuronal cultures were treated with H-8 at doses of 10 µM, starting 1 hour prior to treatment with sodium nitroprusside, starting at the same time as sodium nitroprusside administration, starting 1 hour after sodium nitroprusside administration, starting 4 hours after sodium nitroprusside administration, starting 6 hours after sodium nitroprusside administration, starting 12 hours after sodium nitroprusside administration and starting 24 hours after sodium nitroprusside administration. Protection offered was about the same as obtained for H-7 at the same times of administration in Example II as shown in the FIGURE of the drawing.

EXAMPLE V

Hippocampal neuronal cultures were treated with D-sphingosine at a dose of 10 µM starting 1 hour prior to exposure to sodium nitroprusside or with no sphingosine. The sphingosine increased neuronal cell survival from 22% to 45±4%.

EXAMPLE VI

Hippocampal neuronal cultures were treated with staurosporine at doses of 0.001 µM, 0.01 µM, 0.1 µM and 1.0 µM. Neuronal cell survival increased from 47+3% in cultures treated only with sodium nitroprusside to about 70% at the doses of 0.01 µM and 0.1 µM. At 0.001 µM, survival was about 50%, and at 1 µM, survival was decreased to 42+3%.

EXAMPLE VII

Both common carotid arteries are ligated in two groups of female Sprague-Dawley CFY rats. After 10 minutes, ligations are released and reperfusion is allowed.

In the case of one group, H-7 (20 mg/kg) is administered in the form of a single intraperitoneal injection through a venous catheter 30 minutes after occlusion of the arteries. In the case of the other group, no therapeutic agent is administered.

Histological analysis of stroke volume 24 hours following artery occlusion shows significant reduction in stroke volume for the group administered H-7 compared to the group receiving no treatment.

When H-8 ( 20 mg/kg) or D-sphingosine ( 15 mg/kg) or staurosporine (0.5 mg/kg) is used in place of the H-7, results similar to those obtained with H-7 are obtained.

Variations will be obvious to those skilled in the art. Therefore, the invention is definitely the scope of the claims.

What is claimed is:

1. A method of treatment of a subject with a stroke in progress to reduce the occurrence of neuronal damage, said method comprising administering to said subject within 6 hours of the onset of the stroke a neuronal cell protecting amount of a protein kinase C inhibitor.

2. A method of treatment of a subject with a stroke in progress to reduce the occurrence of neuronal damage, said method comprising administering to said subject within 6 hours of the onset of the stroke a neuronal cell protecting amount of a protein kinase C inhibitor selected from the group consisting of H-7 and H-8.

3. The method of claim 2 wherein, the administering is via a parenteral route.

4. The method of claim 3 wherein the protein kinase C inhibitor is H-7.

5. The method of claim 3 wherein the protein kinase C inhibitor is H-8.

* * * * *